US012097342B2

(12) United States Patent
Mitchell et al.

(10) Patent No.: US 12,097,342 B2
(45) Date of Patent: Sep. 24, 2024

(54) RAPID INSERTION INTEGRATED CATHETER AND METHOD OF USING AN INTEGRATED CATHETER

(71) Applicant: Becton, Dickinson and Company, Salt Lake City, UT (US)

(72) Inventors: James D. Mitchell, Walnut Creek, CA (US); Andrew A. Thoreson, Walnut Creek, CA (US)

(73) Assignee: Becton, Dickinson and Company, Salt Lake City, UT (US)

( * ) Notice: Subject to any disclaimer, the term of this patent is extended or adjusted under 35 U.S.C. 154(b) by 903 days.

(21) Appl. No.: 16/398,020

(22) Filed: Apr. 29, 2019

(65) Prior Publication Data

US 2019/0255294 A1    Aug. 22, 2019

Related U.S. Application Data

(63) Continuation of application No. 15/008,628, filed on Jan. 28, 2016, now Pat. No. 10,376,675.
(Continued)

(51) Int. Cl.
     *A61M 25/06*      (2006.01)
     *A61M 25/00*      (2006.01)
     *A61M 25/01*      (2006.01)

(52) U.S. Cl.
CPC .... *A61M 25/0606* (2013.01); *A61M 25/0029* (2013.01); *A61M 2025/0037* (2013.01); *A61M 25/007* (2013.01); *A61M 25/0102* (2013.01)

(58) Field of Classification Search
CPC .......... A61M 25/0606; A61M 25/0029; A61M 25/007
See application file for complete search history.

(56) References Cited

U.S. PATENT DOCUMENTS

| 1,013,691 A | 1/1912 | Shields |
| 3,225,762 A | 12/1965 | Guttman |

(Continued)

FOREIGN PATENT DOCUMENTS

| DE | 202012006191 U1 | 7/2012 |
| EP | 0653220 A1 | 5/1995 |

(Continued)

OTHER PUBLICATIONS

U.S. Appl. No. 15/008,628, filed Jan. 28, 2016 Final Office Action dated May 30, 2018.
(Continued)

*Primary Examiner* — Dung T Ulsh
(74) *Attorney, Agent, or Firm* — Rutan & Tucker LLP

(57) ABSTRACT

An integrated catheter assembly for rapid vascular insertion including a catheter configured for receipt of a needle and a guidewire; a catheter assembly comprising an integrated assembly comprising a catheter, needle, and guidewire; and a method of rapidly inserting a catheter to obtain vascular access. The catheter includes a central lumen for receiving the needle and guidewire. The lumen includes a distal port and a transverse side port adjacent an intermediate portion thereof which provide open vascular communication from two ports between the central lumen and the vasculature. The needle and guidewire, when integrated with the catheter, extend through the transverse side port wherein a proximal end of the needle extends contiguous to and exterior of a proximal portion of the catheter.

14 Claims, 6 Drawing Sheets

Related U.S. Application Data

(60) Provisional application No. 62/109,403, filed on Jan. 29, 2015.

(56) References Cited

U.S. PATENT DOCUMENTS

| | | |
|---|---|---|
| 3,382,872 A | 5/1968 | Rubin |
| 3,570,485 A | 3/1971 | Reilly |
| 3,890,976 A | 6/1975 | Bazell et al. |
| 4,205,675 A | 6/1980 | Vaillancourt |
| 4,292,970 A | 10/1981 | Hession, Jr. |
| 4,468,224 A | 8/1984 | Enzmann |
| 4,525,157 A | 6/1985 | Vaillancourt |
| 4,581,019 A | 4/1986 | Curelaru et al. |
| 4,594,073 A | 6/1986 | Stine |
| 4,702,735 A | 10/1987 | Luther et al. |
| 4,743,265 A | 5/1988 | Whitehouse et al. |
| 4,766,908 A | 8/1988 | Clement |
| 4,863,432 A | 9/1989 | Kvalo |
| 4,950,252 A | 8/1990 | Luther et al. |
| 4,994,040 A | 2/1991 | Cameron et al. |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,115,816 A | 5/1992 | Lee |
| 5,120,317 A | 6/1992 | Luther |
| 5,158,544 A | 10/1992 | Weinstein |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton |
| 5,306,247 A | 4/1994 | Pfenninger |
| 5,322,512 A | 6/1994 | Mohiuddin |
| 5,328,472 A | 7/1994 | Steinke et al. |
| 5,350,358 A | 9/1994 | Martin |
| 5,358,495 A | 10/1994 | Lynn |
| 5,368,567 A | 11/1994 | Lee |
| 5,378,230 A | 1/1995 | Mahurkar |
| 5,380,290 A | 1/1995 | Makower |
| 5,389,087 A | 2/1995 | Miraki |
| 5,439,449 A | 8/1995 | Mapes et al. |
| 5,443,457 A | 8/1995 | Ginn et al. |
| 5,460,185 A | 10/1995 | Johnson et al. |
| 5,489,271 A | 2/1996 | Andersen |
| 5,573,520 A | 11/1996 | Schwartz |
| 5,683,370 A | 11/1997 | Luther et al. |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,921,971 A | 7/1999 | Agro et al. |
| 5,947,940 A | 9/1999 | Beisel |
| 5,957,893 A | 9/1999 | Luther et al. |
| 5,971,957 A | 10/1999 | Luther et al. |
| 6,159,198 A | 12/2000 | Gardeski et al. |
| 6,206,849 B1 | 3/2001 | Martin et al. |
| 6,228,062 B1 | 5/2001 | Howell et al. |
| 6,475,187 B1 | 11/2002 | Gerberding |
| 6,606,515 B1 | 8/2003 | Windheuser et al. |
| 6,626,869 B1 | 9/2003 | Bint |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,991,625 B1 | 1/2006 | Gately et al. |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 * | 5/2008 | Katoh ............... A61M 25/0084 604/164.13 |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 * | 10/2010 | Healy ............... A61B 17/12022 606/200 |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster |
| 7,967,834 B2 | 6/2011 | Tal et al. |
| 7,976,511 B2 | 7/2011 | Fojtik |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,361,011 B2 | 1/2013 | Mendels |
| 8,372,107 B2 * | 2/2013 | Tupper ............... A61M 16/0472 606/191 |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 * | 11/2014 | Call ..................... A61M 25/09 604/164.01 |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,067,023 B2 | 6/2015 | Bertocci |
| 9,126,012 B2 | 9/2015 | McKinnon et al. |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,445,734 B2 | 9/2016 | Grunwald |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutillette et al. |
| 9,820,845 B2 | 11/2017 | von Lehe et al. |
| 9,861,383 B2 | 1/2018 | Clark |
| 9,872,971 B2 | 1/2018 | Blanchard |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,981,113 B2 | 5/2018 | Bierman |
| 10,010,312 B2 | 7/2018 | Tegels |
| 10,065,020 B2 | 9/2018 | Gaur |
| 10,086,170 B2 | 10/2018 | Chhikara et al. |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |

(56) References Cited

U.S. PATENT DOCUMENTS

| | | |
|---|---|---|
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 11,759,607 B1 | 9/2023 | Biancarelli |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1* | 5/2003 | Jang ............... A61M 25/104 600/585 |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | Defonzo |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully |
| 2015/0011834 A1* | 1/2015 | Ayala ............... A61B 17/0218 29/428 |
| 2015/0080939 A1 | 3/2015 | Adams et al. |
| 2015/0094653 A1 | 4/2015 | Pacheco et al. |
| 2015/0112307 A1* | 4/2015 | Margolis ......... A61M 25/09041 604/510 |
| 2015/0112310 A1 | 4/2015 | Call et al. |
| 2015/0126930 A1 | 5/2015 | Bierman et al. |
| 2015/0148595 A1* | 5/2015 | Bagwell ............ A61B 17/3403 600/104 |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0242661 A1* | 8/2016 | Fischell ............... A61B 5/4035 |
| 2016/0256101 A1* | 9/2016 | Aharoni ............... A61B 5/0086 |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1* | 6/2017 | Urbanski ............... A61B 17/34 |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0021640 A1 | 1/2019 | Burkholz et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |

(56) References Cited

U.S. PATENT DOCUMENTS

| | | |
|---|---|---|
| 2019/0201665 A1 | 7/2019 | Turpin |
| 2019/0209812 A1 | 7/2019 | Burkholz et al. |
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0126064 A1 | 4/2022 | Tobin et al. |
| 2022/0193376 A1 | 6/2022 | Spataro et al. |
| 2022/0193377 A1 | 6/2022 | Haymond et al. |
| 2022/0193378 A1 | 6/2022 | Spataro et al. |
| 2022/0323723 A1 | 10/2022 | Spataro et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0233814 A1 | 7/2023 | Howell et al. |
| 2024/0009427 A1 | 1/2024 | Howell et al. |
| 2024/0050706 A1 | 2/2024 | Howell et al. |
| 2024/0198058 A1 | 6/2024 | Howell et al. |

FOREIGN PATENT DOCUMENTS

| | | | |
|---|---|---|---|
| EP | 0730880 | A1 | 9/1996 |
| EP | 2061385 | A1 | 5/2009 |
| EP | 1458437 | B1 | 3/2010 |
| EP | 2248549 | A2 | 11/2010 |
| EP | 2319576 | A1 | 5/2011 |
| EP | 2366422 | A1 | 9/2011 |
| EP | 2486880 | A2 | 8/2012 |
| EP | 2486881 | A2 | 8/2012 |
| EP | 2486951 | A2 | 8/2012 |
| EP | 2512576 | A2 | 10/2012 |
| EP | 2152348 | B1 | 2/2015 |
| EP | 3473291 | A1 | 4/2019 |
| EP | 3093038 | B1 | 5/2019 |
| EP | 2260897 | B1 | 9/2019 |
| EP | 3693051 | A1 | 8/2020 |
| GB | 1273547 | A | 5/1972 |
| JP | 2004248987 | A | 9/2004 |
| JP | 2008054859 | A | 3/2008 |
| WO | 9421315 | A1 | 9/1994 |
| WO | 9532009 | A2 | 11/1995 |
| WO | 9844979 | A1 | 10/1998 |
| WO | 9853871 | A1 | 12/1998 |
| WO | 9912600 | A1 | 3/1999 |
| WO | 99/26681 | A1 | 6/1999 |
| WO | 00/06221 | A1 | 2/2000 |
| WO | 0054830 | A1 | 9/2000 |
| WO | 2003008020 | A1 | 1/2003 |
| WO | 2003057272 | A2 | 7/2003 |
| WO | 03068073 | A1 | 8/2003 |
| WO | 2003066125 | A2 | 8/2003 |
| WO | 2005/096778 | A2 | 10/2005 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011/109792 | A1 | 9/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012/154277 | A1 | 11/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015077560 | A1 | 5/2015 |
| WO | 2015/168655 | A2 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016/178974 | A1 | 11/2016 |
| WO | 2016176065 | A1 | 11/2016 |
| WO | 2016187063 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/050576 | A1 | 3/2019 |
| WO | 2019146026 | A1 | 8/2019 |
| WO | 2019199734 | A1 | 10/2019 |
| WO | 2020014149 | A1 | 1/2020 |
| WO | 2020069395 | A1 | 4/2020 |
| WO | 2020109448 | A1 | 6/2020 |
| WO | 2020113123 | A1 | 6/2020 |
| WO | 2021050302 | A1 | 3/2021 |
| WO | 2021062023 | A1 | 4/2021 |
| WO | 2021077103 | A1 | 4/2021 |
| WO | 2021081205 | A1 | 4/2021 |
| WO | 2021086793 | A1 | 5/2021 |
| WO | 2021/236950 | A1 | 11/2021 |
| WO | 2022031618 | A1 | 2/2022 |
| WO | 2022094141 | A1 | 5/2022 |
| WO | 2022/133297 | A1 | 6/2022 |

(56) References Cited

FOREIGN PATENT DOCUMENTS

| | | | |
|---|---|---|---|
| WO | 2022-140406 | A1 | 6/2022 |
| WO | 2022140429 | A1 | 6/2022 |
| WO | 2022/217098 | A1 | 10/2022 |
| WO | 2023014994 | A1 | 2/2023 |
| WO | 2023049498 | A1 | 3/2023 |
| WO | 2023049505 | A1 | 3/2023 |
| WO | 2023049511 | A1 | 3/2023 |
| WO | 2023049519 | A1 | 3/2023 |
| WO | 2023049522 | A1 | 3/2023 |
| WO | 2023146792 | A1 | 8/2023 |

OTHER PUBLICATIONS

U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
U.S. Appl. No. 17/031,478, filed Sep. 24, 2020 Non-Final Office Action dated May 11, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
PCT/US2022/039614 filed Aug. 5, 2022 International Search Report and Written Opinion dated Dec. 22, 2022.
PCT/US2022/044848 filed Sep. 27, 2022 International Search Report and Written Opinion dated Feb. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/326,017, filed May 20, 2021 Notice of Allowance dated Jul. 3, 2023.
U.S. Appl. No. 17/360,694, filed Jun. 28, 2021 Restriction Requirement dated Jul. 20, 2023.
U.S. Appl. No. 17/390,682, filed Jul. 30, 2021 Final Office Action dated Jul. 27, 2023.
U.S. Appl. No. 17/392,061, filed Aug. 2, 2021 Non-Final Office Action dated Jul. 17, 2023.
PCT/US2022/024085 filed Apr. 8, 2022 International Search Report and Wirtten Opinion dated Sep. 12, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/039084 filed Jun. 25, 2021 International Search Report and Written Opinion dated Jan. 10, 2022.
PCT/US2021/044029 filed Jul. 30, 2021 International Search Report and Written Opinion dated Dec. 9, 2021.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
PCT/US2021/057135 filed Oct. 28, 2021 International Search Report and Written Opinion dated Mar. 11, 2022.
PCT/US2021/064671 filed Dec. 21, 2021 International Search Report and Written Opinion dated May 27, 2022.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/513,789, filed Oct. 28, 2021 Restriction Requirement dated Oct. 3, 2023.
U.S. Appl. No. 17/557,924, filed Dec. 21, 2021 Non-Final Office Action dated Nov. 3, 2023.
PCT/US2021/057135 filed Oct. 28, 2021 International Preliminary Report on Patentability dated May 2, 2023.
PCT/US2023/011173 filed Jan. 19, 2023 International Search Report and Written Opinion dated May 22, 2023.
U.S. Appl. No. 17/156,252, filed Jan. 22, 2021 Notice of Allowance dated Apr. 24, 2023.
U.S. Appl. No. 17/240,591, filed Apr. 26, 2021 Non-Final Office Action dated Jun. 8, 2023.
U.S. Appl. No. 17/358,504, filed Jun. 25, 2021 Restriction Requirement dated Jun. 7, 2023.
U.S. Appl. No. 17/392,061, filed Aug. 2, 2021 Restriction Requirement dated Mar. 30, 2023.
U.S. Appl. No. 17/234,611, filed Apr. 19, 2021 Non-Final Office Action dated Apr. 23, 2024.
U.S. Appl. No. 17/234,611, filed Apr. 19, 2021 Restriction Requirement dated Jan. 18, 2024.
U.S. Appl. No. 17/240,591, filed Apr. 26, 2021 Advisory Action dated Feb. 22, 2024.
U.S. Appl. No. 17/358,504, filed Jun. 25, 2021 Final Office Action dated Mar. 13, 2024.
U.S. Appl. No. 17/360,694, filed Jun. 28, 2021 Non-Final Office Action dated Feb. 14, 2024.
U.S. Appl. No. 17/392,061, filed Aug. 2, 2021 Advisory Action dated Feb. 14, 2024.

(56) References Cited

OTHER PUBLICATIONS

U.S. Appl. No. 17/392,061, filed Aug. 2, 2021 Non-Final Office Action dated Apr. 23, 2024.
U.S. Appl. No. 17/513,789, filed Oct. 28, 2021 Non-Final Office Action dated Jan. 9, 2024.
U.S. Appl. No. 17/554,978, filed Dec. 17, 2021 Non-Final Office Action dated Apr. 19, 2024.
U.S. Appl. No. 17/557,924, filed Dec. 21, 2021 Final Office Action dated Feb. 29, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Notice of Allowance dated Jul. 17, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/513,789, filed Oct. 28, 2021 Final Office Action dated Jul. 9, 2024.

* cited by examiner

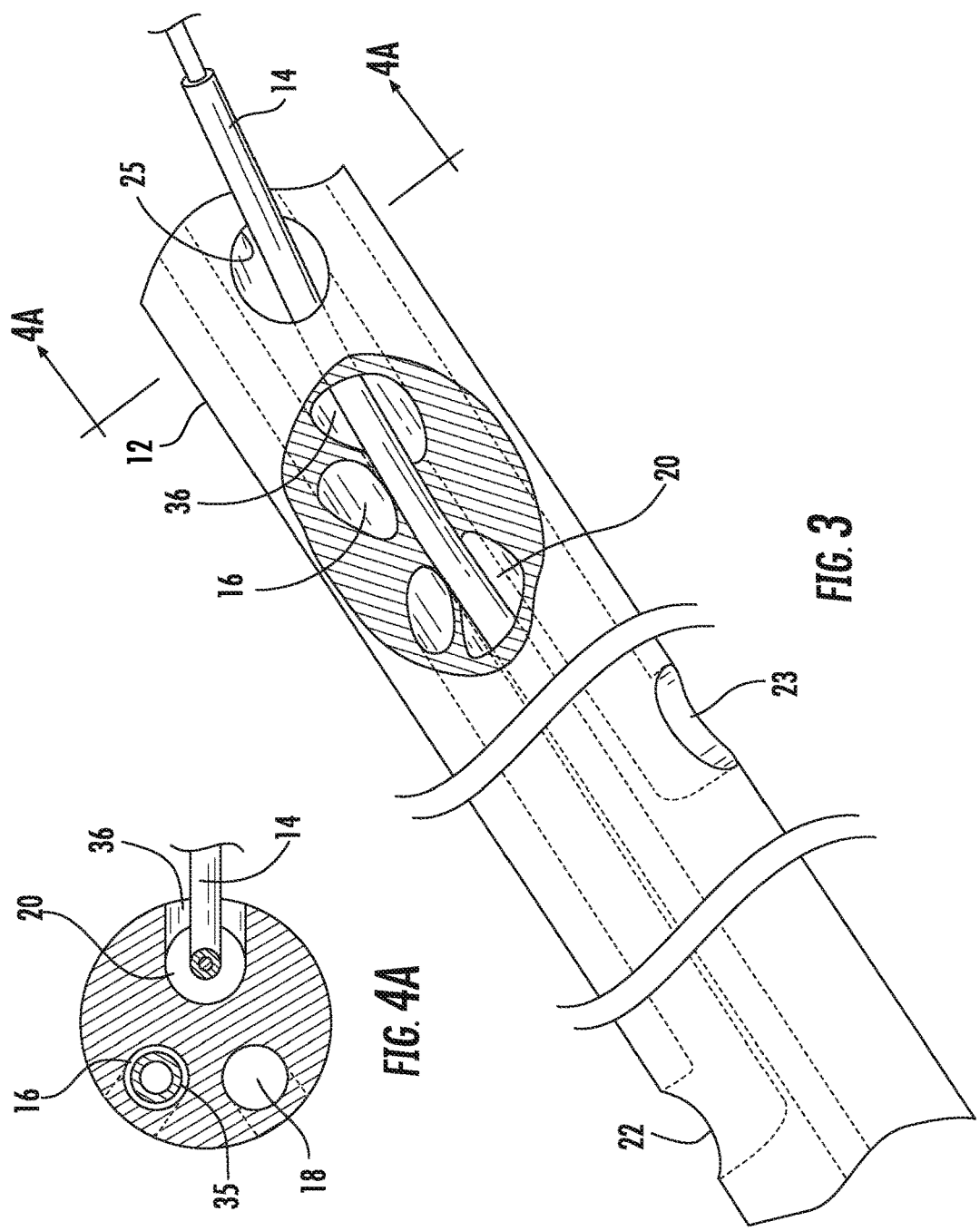
FIG. 3
FIG. 4A
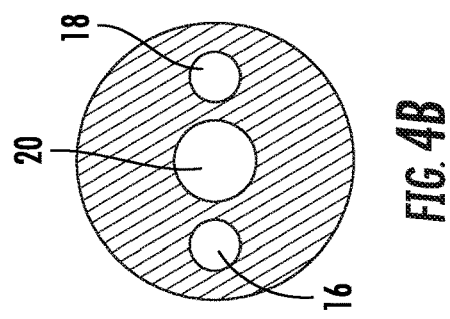
FIG. 4B
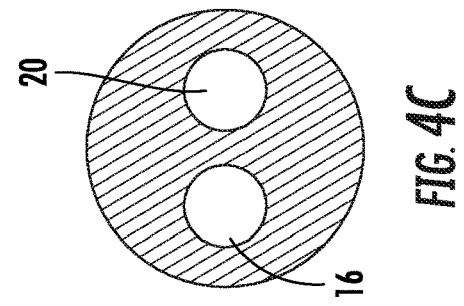
FIG. 4C

RAPID INSERTION INTEGRATED CATHETER AND METHOD OF USING AN INTEGRATED CATHETER

CROSS-REFERENCE TO RELATED APPLICATION

This application is a continuation of and claims priority to U.S. application Ser. No. 15/008,628 filed Jan. 28, 2016 which claims priority to U.S. Provisional Patent Application Ser. No. 62/109,403 filed Jan. 29, 2015, the disclosures of which are hereby incorporated by reference.

FIELD OF THE INVENTION

The present invention is directed to a venous catheter and the method of using the venous catheter, generally, and, more specifically, to a venous catheter assembly with a catheter configured for receipt of an integrated needle and guidewire for rapid insertion and the method of using the integrated catheter.

BACKGROUND OF THE INVENTION

Venous catheters, including central, peripheral, and so-called "midline" or extended-dwell peripheral venous catheters, are used in the medical environment to provide intravenous vascular access. Vascular access by venous catheters provides an expedient and highly effective means for drug administration, other fluid administration, chemotherapy, blood sampling, blood pressure monitoring, and parenteral nutrition, for example. These procedures often require that the catheter be left indwelling in the patient for an extended period of time. In a hospital setting, venous catheters are widely used in emergency departments, intensive care units, and operating rooms. In such settings, it is imperative that the venous catheters be very quickly and correctly positioned intravenously within the patient to obtain vascular access particularly in critical situations requiring rapid administration of medicines.

Highly effective and commonly used venous catheters are triple lumen catheters which are intravenously positioned within any venous structure, including the internal/external jugular, subclavian, or, femoral vein. Triple lumen catheters commonly include a central lumen which extends from the proximal end adjacent the user to the distal end which is positioned within the venous system. Two additional lumens may extend from the proximal end and terminate at a location adjacent to, but proximally removed from, the distal end of the catheter and terminate in open side ports. U.S. Pat. No. 7,311,697 B2 is an exemplary triple lumen catheter.

A widely accepted and commonly used percutaneous entry technique used to obtain access to the venous system of a patient requiring a venous catheter is a landmark guided technique known as the Seldinger technique. The Seldinger technique involves multiple steps which must be employed in medical conditions necessitating expedient placement of a line, such as in an emergency setting. In the Seldinger technique, the, physician makes an oblique entry with a hollow needle through the patient's skin, at a peripheral location using landmark guidance, and into a vein. The commonly used Seldinger technique is most often employed in combination with imaging guidance (e.g., ultrasound). Landmark guidance techniques involve visually or palpably locating anatomical landmarks for locating the targeted vein. For example, for subclavian vein entry, the landmark guided technique includes locating the junction of the middle and proximal third of the clavicle and inserting the needle at that location.

A blunt guidewire is then passed through the central lumen of the needle, and then the needle is withdrawn and removed leaving the guidewire within the vein. Next, a dilating device s passed over the guidewire to slightly enlarge the tract originally produced by the needle and, if warranted, multiple dilators having varying gauge, may be utilized, in a process called serial dilation. The dilator is then removed, leaving the guidewire within the vein. The catheter is then passed along the length and over the guidewire until positioned within the vein. Alternatively, use of a peel-away sheath may be used for placement of a catheter. The sheath may be utilized in conjunction with a dilator (also known as an introducer in this setting) for over-the-wire placement into the desired vessel. Once the sheath is within the vessel, the inner dilator (introducer) and wire are removed, allowing for placement of the catheter through the sheath's lumen. The sheath is then removed in a peel-away fashion, leaving only the catheter behind in the vessel. Blood may then be withdrawn from a catheter port to confirm the catheter placement within the vein. The guidewire is then removed from the vein.

With regard to initial percutaneous placement of the catheter, it is important to quickly position the venous catheter within the appropriate vein. This is imperative not only for the comfort of the patient, but also to achieve successful medical outcomes. Risks associated with incorrect catheter placement and multiple attempts at placement of the catheter include an increased risk of catheter related blood-stream infections from loss of sterility. In extreme instances, improper catheter placement may be injurious to adjacent structures such as the carotid artery, with serious consequences such as hemorrhage, stroke, or pseudo aneurysm formation. It is, thus, recognized that catheter placement may be assisted by utilizing real-time: ultrasound imaging techniques in order to minimize such complications. Additionally, high quality, portable ultrasound units have become more regularly available to physicians, thereby further facilitating the use of ultrasound assisted venous catheter placement. An exemplary method employing ultrasound guided central venous catheter placement is U.S. Publication. No. WO 2014006403 A1. More recently, vascular access devices have expanded to include midline catheters, or extended dwell peripheral intravenous lines. Midline catheters are longer and more durable than traditional peripheral intravenous catheters. Different than central catheters, midline catheters do not terminate in the vena cava or right atrium. However, they are typically placed in the larger veins of the upper extremity such as the radial, cephalic, median, brachial or basilicvein. Owing to their durability and location, midline catheters can remain in place longer than the traditional 2-3 days for a peripheral intravenous catheter without the same risks of infiltration and infection. Additionally, because of their size and insertion location, midline catheters are inserted using a combination needle puncture and over-the-wire access and insertion procedure. Although this differs somewhat from the Seldinger technique used for central catheters, it lends itself to benefit from the design and procedure described herein.

SUMMARY OF THE INVENTION

The present invention overcomes shortcomings of the prior art by providing a catheter assembly having a catheter configured for receipt of a needle and guidewire along an outer side surface for rapid insertion of the catheter assembly. Preferably, the venous placement of the catheter is facilitated with ultrasound guided techniques. The integrated catheter, that is, a catheter configured for receipt of a needle and guidewire which, according to one aspect, may be pre-assembled, includes at least a lumen for receipt of a transversely inserted needle which extends axially along the length of a distal portion of the lumen. The lumen extends from the proximal to the distal end of the catheter. Preferably one or more additional lumens, or "non-needle" lumens, are provided and extend from the catheter proximal end and terminate at side ports adjacent the catheter distal end. An additional side port, positioned proximal to the one or more non-needle side ports, is also provided on the catheter body and provides a port for receipt of the needle from an outer side surface of the catheter body, substantially in a transverse direction. The needle receiving side port defines the terminal end of a transverse channel which provides an open channel from the needle receiving side port to the needle lumen. According to another aspect of the present invention, the catheter may, therefore, be pre-assembled so as to include the needle and guidewire wherein the needle and the guidewire extend adjacent to and exterior of a proximal side portion of the catheter.

The method of using the catheter assembly according to the present invention includes the steps of pre-assembling the needle and guidewire within the catheter's needle side port to form an integrated catheter assembly; inserting the needle into the patient's venous system, preferably using ultrasound guidance; introducing the guidewire distally along the length of the needle and into the vessel; removing the needle; advancing the catheter distally along the length of the guidewire until positioned within the venous system; removing the guidewire; and confirming proper placement of the catheter. It is also within the scope of the presently described method to advance or remove the needle and guidewire together in the same method step as opposed to independently removing each. Accordingly, the present invention obviates several method steps of the prior Seldinger technique. Specifically, the catheter assembly according to preferred embodiments, utilizes ultrasound guidance to prevent inaccurate catheter placement. Medical complications are minimized and proper positioning of the catheter is expeditiously accomplished for rapid medical administration. Moreover, the integrated catheter assembly obviates the need for the additional steps of dilating the incision with a dilator(s) in that the catheter of the present invention is self-dilating. According to one aspect of the invention, use of stylets in multi-lumen catheters are selectively used to enhance the rigidity of the assembly and its ability to self-dilate. The integrated catheter of the present invention provides a pre-assembled guidewire within the needle thereby eliminating the need to thread the guidewire though the needle once vascular access is obtained and threading the catheter over the guidewire.

Numerous benefits are achieved by the integrated catheter assembly according to the present invention including a novel catheter for transversely receiving a needle and guidewire which may be pre-assembled in an integrated catheter assembly. One significant benefit is a marked decrease in the time required to percutaneously position the catheter within in a vessel lumen to achieve endovascular access with the catheter due to the elimination of conventional method steps involving the exchange of individual components according to the Seldinger technique. This allows for rapid insertion of the catheter and, hence, rapid administration of medicines or other substances. The pre-assembled integrated catheter assembly obviates the need to provide the discrete units of: catheter, needle, guidewire and a dilator. This eliminates the step of inserting the needle, threading the guidewire within the needle, and positioning the catheter along the guidewire. There is also a decreased risk of the loss of venous access which may occur with prior art methods of exchanging multiple components. The integrated catheter assembly of the present invention also obturates the catheter lumens and prevents complications of air embolism and limits blood loss. The additional needle side port of the catheter, once vacated by the needle and guidewire, beneficially provides an additional port for more rapid administration of greater amounts of medicines or other fluids and provides an additional administration port should the distal port become occluded. The integrated catheter assembly also does not require a separate dilator as the configuration of the various components presents a self-dilating integrated catheter assembly. By decreasing the number of method steps necessary for effective catheter insertion and by eliminating multiple assembly component exchanges over the guidewire, the catheter assembly and method according to the present invention beneficially reduces the risk of catheter related infection; thereby resulting in improved medical outcomes. These and other objectives are met by the present invention.

BRIEF DESCRIPTION OF THE DRAWINGS

FIG. 3 is an enlarged, partially broken away, view of a needle side port according to the present invention;

FIG. 4A is a cross sectional view of the catheter taken along line 4A in FIG. 3;

FIG. 4B is a cross sectional view according to an alternative aspect of the present invention;

FIG. 4C is a cross sectional view according to another alternative aspect of the present invention;

DETAILED DESCRIPTION OF THE INVENTION

The present invention will now be described in detail hereinafter by reference to the accompanying drawings. The invention is not intended to be limited to the embodiments described; rather, this detailed description is provided to enable any person skilled in the art to make and practice the invention.

Figure 1:
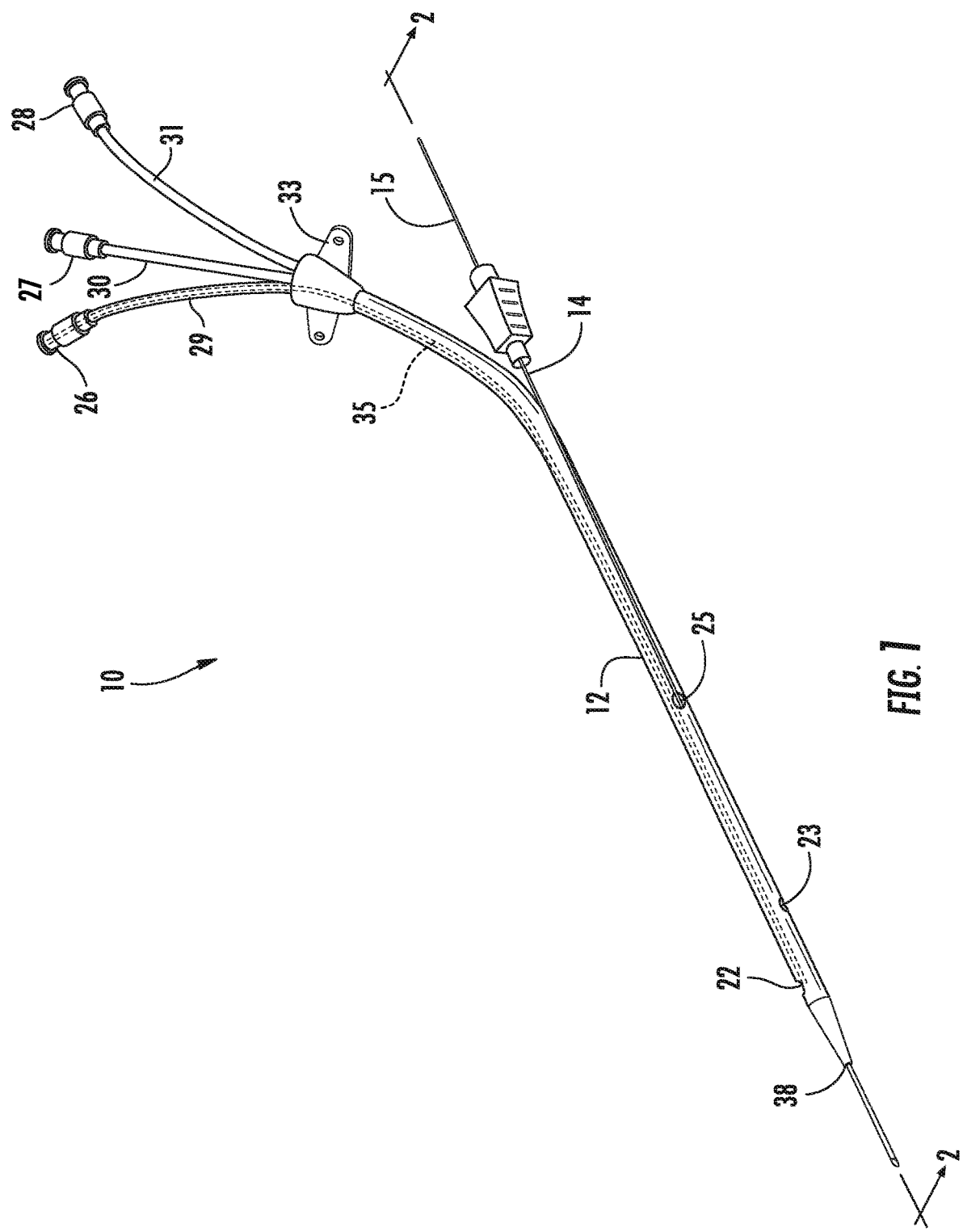
FIG. 1 is a perspective view of the integrated catheter according to the present invention.

The venous catheter assembly 10, as shown in FIG. 1, is used for surgical procedures in which a catheter is inserted percutaneously into the blood vessel for treatment. This treatment may include, for example, the administration of medicine or other fluids, blood pressure monitoring, and/or blood sampling. This invention is not limited to these uses, as it is within the scope of the present invention to provide a catheter for intravascular access, including, but not limited to, a central, midline or peripheral venous catheter. As is known in the art, the venous catheter as described herein may be used with any cavitary or luminal structure, including any vein. For the sake of discussion, the detailed description herein addresses use of the catheter assembly with any vein. As used herein, the terms "proximal" and "distal" are used to refer to the axial ends of the catheter assembly and various components. The term "proximal end" refers to the end closely adjacent the user of the assembly and the term "distal end" refers to the end of the catheter assembly that is percutaneously inserted into the patient, i.e., adjacent the needle tip. According to the invention illustrated in the various Figures, excluding horizontal cross-sections, the proximal end is toward the right and the distal end is toward the left. Also as used herein, the "axial direction" refers to the longitudinal axis of the catheter from the proximal end to the distal end. The term "transverse" direction refers to a direction which intersects the longitudinal axis, at any angle.

The venous catheter assembly 10 includes, generally, a novel catheter 12, a needle 14, and a guidewire 15. The catheter assembly 10 illustrated includes three lumens 16, 18, and 20, shown in FIG. 2. Each lumen provides a passageway for the ingress of fluids to or the egress of blood from the vascular system. Although venous catheters may have only a single lumen, such as lumen 20 which extends longitudinally from the proximal end adjacent the user to the distal end for venous insertion, it is more common to provide more than one lumen. Two or three (or more) lumen catheters are commonly utilized for diverse uses of a venous line. Multiple lumens also provide alternative administration or aspiration lumens should more than one lumen be used simultaneously or should one of the other lumens become occluded. The present invention relates to such single or multiple lumen catheters and a catheter assembly including the catheter. FIG. 4 illustrates a triple lumen catheter 12 as described herein in connection with the various other Figures. FIG. 4A, taken along line 4A-4A in FIG. 3, illustrates the cross-sectional view of the catheter assembly 10 according to one aspect of the present invention. FIG. 4A also illustrates a stylet 35 in one lumen, 16, which may selectively be positioned in any of the lumens. (It is noted that FIG. 3 does not include the stylet 35.) FIGS. 4B and 4C illustrate alternative aspects of the present invention. FIG. 4B illustrates a triple lumen catheter 12 including lumens 16, 18 and 20 which are differently positioned within the catheter 12. This is exemplary of various lumen positions contemplated by the present invention. FIG. 4C illustrates a double lumen catheter including the needle lumen 20 and one additional non-needle lumen 16. According to any of these aspects, a stylet 35 may be inserted into one or more of the lumens. Moreover, any known method of providing increased column strength may be utilized without departing from the spirit and scope of the present invention. This includes providing strengthening materials such as beads, coils or wires into the "dead space" (spaced within the catheter exterior to any of the lumens). According to the present invention, it may be desirable to include the stylet 35 into either or all of the non-needle receiving lumens, 16 and/or 18, which extends beyond the lumen side port 22 and/or 23.

The lumen 20 extends the length of the catheter and is configured to receive the needle 14. The one or more additional lumens, 16 and 18 as shown, are referred to as "non-needle lumens". The non-needle lumens 16 and 18 each terminate at a respective side port 22, 23, defined by the catheter outer wall. According to the present invention, a needle side port 25 is also provided as will be described in greater detail below. The side ports 22, 23 of the non-needle lumens 16, 18 establishes intravenous communication of the catheter lumens 16, 18. As such, medicine and/or fluids may be introduced into the catheter, pass through the lumens, and exit the side ports to the vessel in which the catheter has been placed.

Preferably, side ports 22, 23 and 25 are longitudinally separated along the length of the catheter 12. As shown, the needle port 25 is positioned proximal to the non-needle ports 22, 23. This is exemplary, and it is within the scope of the present invention for the needle port to be distally positioned relative to one or more of the other side ports. The distance between the ports 22, 23, 25 is selected in proportion to the catheter's French size so as to axially separate distribution ports wherein multiple fluids may be substantially simultaneously administered through the various lumens. Additionally, the side ports are preferably oriented in a spiral or helical configuration along the catheter body to further separate distribution ports and to sustain the structural integrity of the catheter, particularly during insertion thereof. This configuration also is preferable to avoid multiple ports from becoming simultaneously occluded such as contact with a vessel wall or other intravascular structure. It is envisioned, however, that the various ports may be positioned along that same general side of the catheter and linearly as well.

Figure 2:
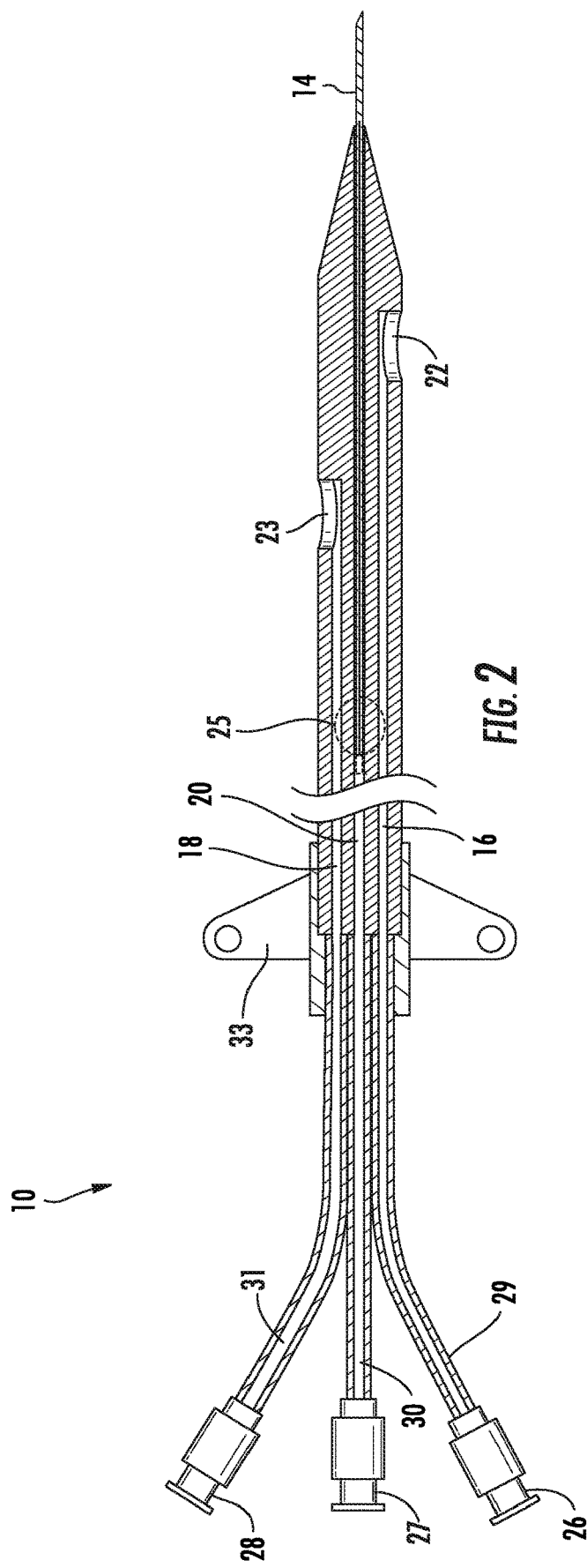
FIG. 2 is a cross-sectional view taken along line 2-2 of FIG. 1.

The venous catheter assembly 10 of the illustrated embodiment is a triple lumen catheter. It is within the scope of the present invention, however, to provide a single lumen 20 and one or more additional non-needle lumens. As shown in FIG. 2, the lumen 20 extends from the proximal end to the distal end of the catheter 12 body. Two additional lumens 16, 18 are shown and each lumen is independent and not communicative with the other lumens 16, 18, 20. The catheter 12 further includes, in the illustrated embodiment, entry ports 26, 27, and 28 which communicate with a respective lumen 16, 18, 20 for the administration of or extraction of fluids or blood. As is known in the art, entry ports 26, 27, 28 may be manipulated to selectively occlude communication of the exterior environment with the lumens. Extension tubes 29, 30, 31 connect the entry ports to a respective lumen and may be of any desired length. Side clamps, not shown, may also be provided along the extension tubes as is known in the art to control the fluid flow through the lumen. As to one aspect of the present invention, a hub 33 joins distal ends of the extension tubes 29, 30, 31 to the proximal end of the catheter 12 to establish communication between the extension tubes and the respective lumen. The hub 33 is provided with a pair of radially extending wings which are advantageously used to further secure the catheter in place with sutures or adhesive-type devices applied to the skin (such as StatLock®).

A stylet 35 in the form of flexible or semi-rigid material, as shown, is provided within one or both non-needle lumens 16, 18 according to an alternative aspect of the present invention. The stylet 35 may likewise be positioned with the needle-receiving lumen 20. Such materials that may be utilized for the stylet include, but are not limited to, solid, hollow, or wire-like plastic or other polymeric material or metal or other alloy (for example, in a tubular configuration). As shown in FIGS. 1 and 4A, lumen 16 comprises a stylet 35 which is selectively inserted into the lumen 16 to improve rigidity in the form of column strength to the catheter. The amount of column strength required and, hence the number and kind of stylet(s), may vary from patient to patient and procedure to procedure. As shown, the stylet 35 extends substantially the axial length of the catheter 12, but it is within the scope of the present invention to provide a stylet within only a portion of the lumen 16. The stylet 35 provides structural rigidity to the catheter 12 which is important as the catheter 12 is percutaneously advanced through the skin, subcutaneous tissues, and blood vessel wall. This is referred to as the catheters "pushability", or ability to possess sufficient rigidity so as to be percutaneously inserted and yet not too rigid so as to cause injury to the vein or surrounding perivascular structures. Moreover, the catheter 12 must remain substantially flexible and pliable for insertion into the venous system. While not being bound by any particular theory, it is believed that the stylet as shown, in combination with the catheter 12 construction, provides sufficient column strength to the catheter 12 for its application while also providing sufficient flexibility for introduction of the catheter into the venous system of a patient. The stylet is to be removed once the catheter is secured in place.

The catheter body 12 defines a novel side port 25 which, as shown, is positioned along the length of the catheter at a position proximal to the non-needle lumen side ports 22, 23. A transverse channel 36 extends from the side port 25 to the lumen 20 to provide open communication there between. As shown in FIG. 3, the transverse channel 36 is angularly positioned relative to the lumen axis and extends transversely with respect thereto. More specifically, the transverse channel 36 as shown extends at an acute angle relative the lumen axis. It is preferred that the angular orientation of the transverse channel 36 be at least approximately 90 degrees or less due to the envisioned angle of needle insertion. The side port 25 is sized, configured and positioned to receive the needle 14.

The catheter assembly 10 may be advantageously provided to include the catheter 12 with a pre-assembled needle 14 and guidewire 15 inserted within the side port 25. As such, the needle 14 extends within a distal portion of the lumen 20 and out the distal tip 38 of the catheter 12. Accordingly, a proximal portion of the needle 14 is contiguous with an outer proximal portion of the catheter, transverse to the lumen axis, while a distal portion of the needle 14 extends co-axially within the lumen 20.

Figure 9:
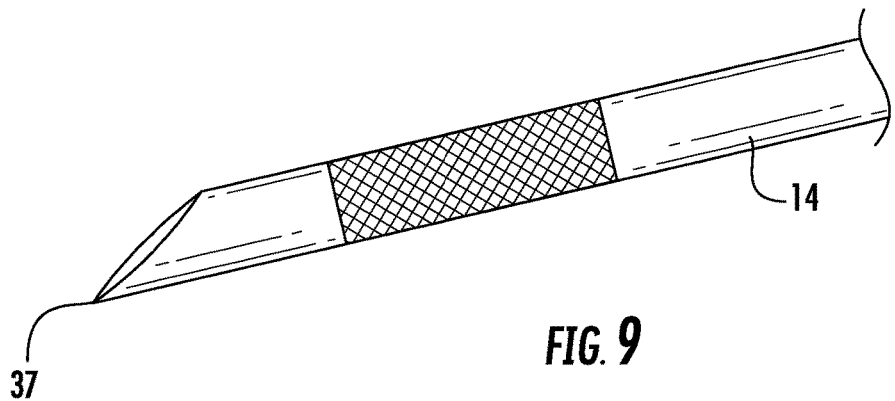
FIG. 9 is an enlarged perspective view of the needle tip.

As shown in FIG. 9, the needle 14 has an insertion tip 37 which is preferably beveled. The gradual taper of the bevel facilitates dilation through the soft tissues and vessel wall for the needle 14 and simultaneously dilates the soft tissues and vessel wall for the catheter 12 insertion. The needle 14 is hollow and may be formed of a surgical grade stainless steel, such as an 18-22 gauge, as is common in the art. As shown in the various Figures, the needle 14 is inserted (preferably prior to use) into the needle side port 25, extends along the length of the transverse channel 36 and enters the lumen 20. The needle 14 extends through a distal aperture on the distal tip 38 of the catheter 12. The distal aperture is preferably sized in accordance with the needle gauge wherein only minimal tolerances are provided for smooth trackability. Preferably, the needle 14 includes an etched portion in the form of a band to provide improved visualization when using ultrasound guidance.

Figure 10:
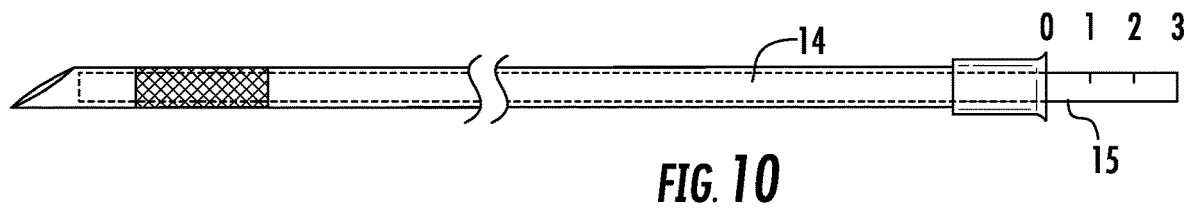
FIG. 10 is a perspective view, partially broken away, of the needle and guidewire.

As shown in FIG. 10, the guidewire 15 extends along the length of the hollow needle 14. The proximal end of the guidewire preferably includes visible marks at regular intervals, for example, 1 cm, to indicate the depth of the wire. This avoids placement too deep within the vasculature, but of sufficient depth for catheter placement. The guidewire 15 may be formed of material known in the art, such as surgical grade wire such as a composite with a nitinol core to provide a blend of stiffness and flexibility, for effective torque control and venous navigation.

Figure 11:
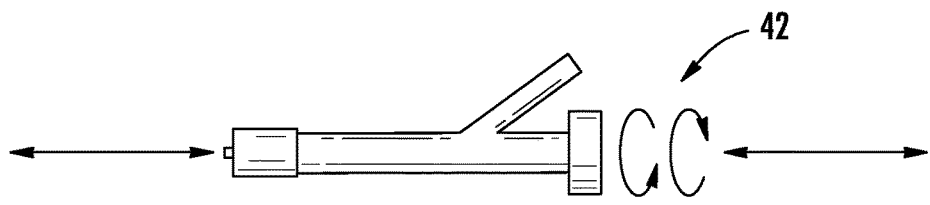
FIG. 11 is a hemostatic valve according to another aspect of the present invention.

FIG. 11 depicts a hemostatic valve 42 which may optionally be used as part of the integrated catheter assembly to facilitate aspiration of the side port 25 to confirm intravascular placement of the catheter 12. The hemostatic valve 42 may be particularly beneficial if ultrasound guided placement is not utilized. The hemostatic valve 42 may be fastened to the proximal hub 33 in a known manner and positioned over the guidewire.

The catheter 12 is a disposable, single use device that is made of a biocompatible material. The stylet, needle, and guidewire may be made of known materials, such as steel, nitinol, or a composition including one or both of these. As set forth above, the stylet 35 may be formed of a plastic or other polymeric or metallic material. The guidewire 15, according to one aspect, is formed of a flexible material to accommodate anatomical complications such as complex and tortuous vasculature. Commonly used materials are a polymeric coated or metallic wire.

Figure 5:
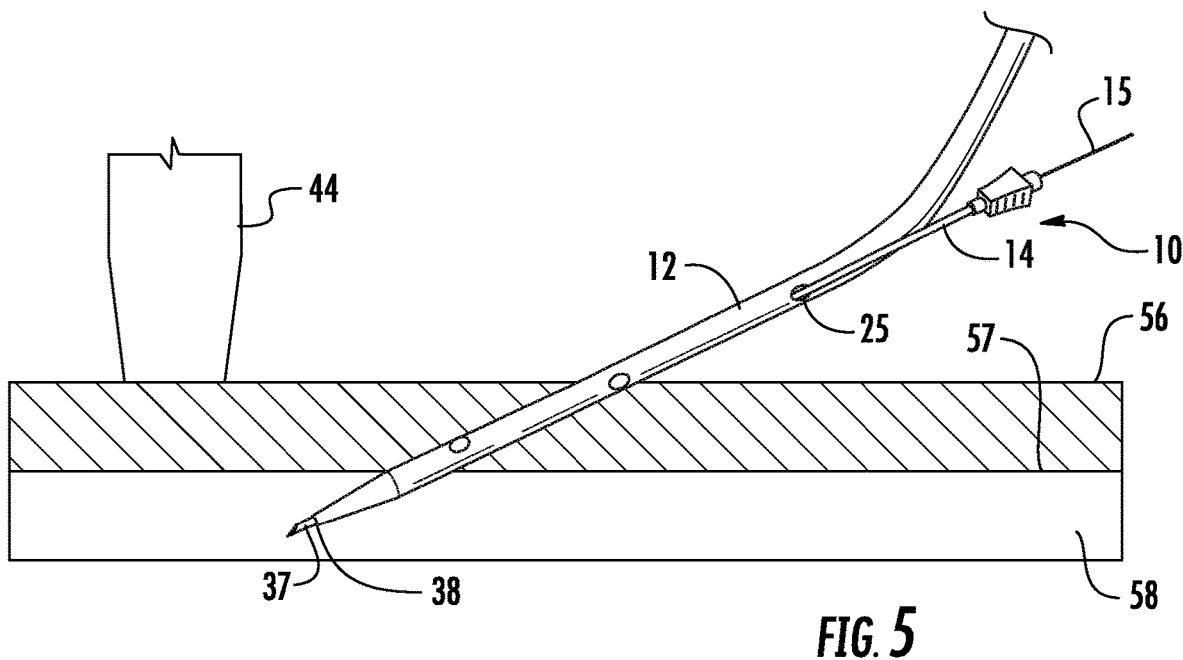
FIG. 5 is a schematic illustration of a method step of inserting the integrated catheter.
Figure 6:
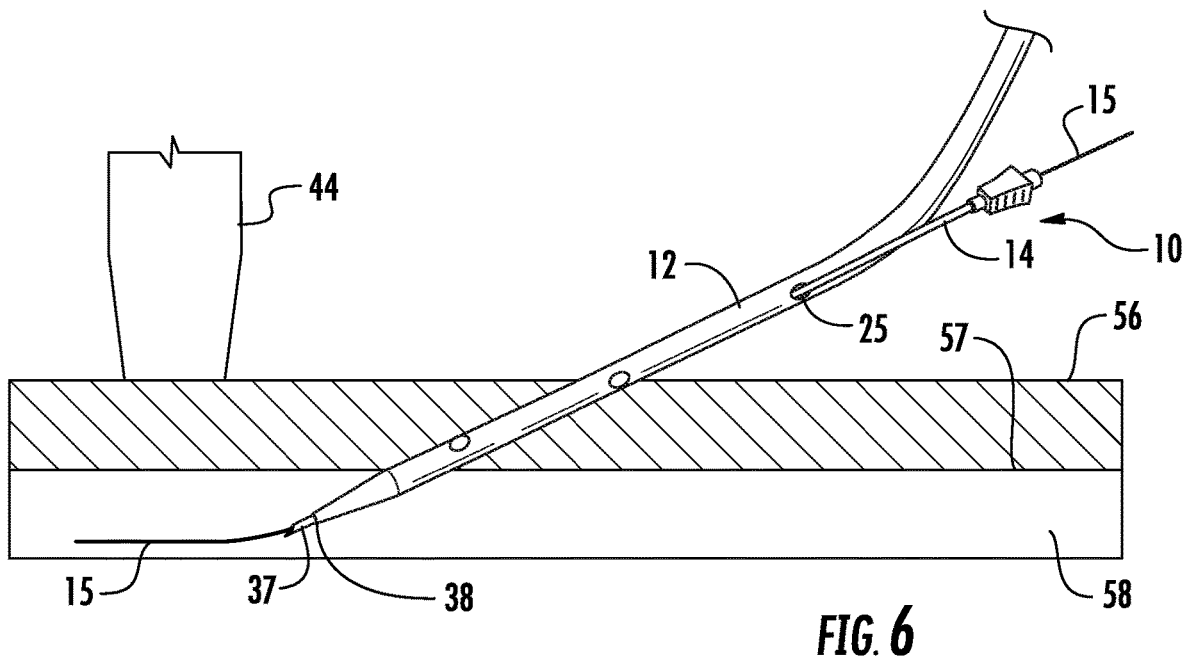
FIG. 6 is a schematic illustration of a subsequent method step of endovascular deployment of the guidewire into the vessel lumen.
Figure 7:
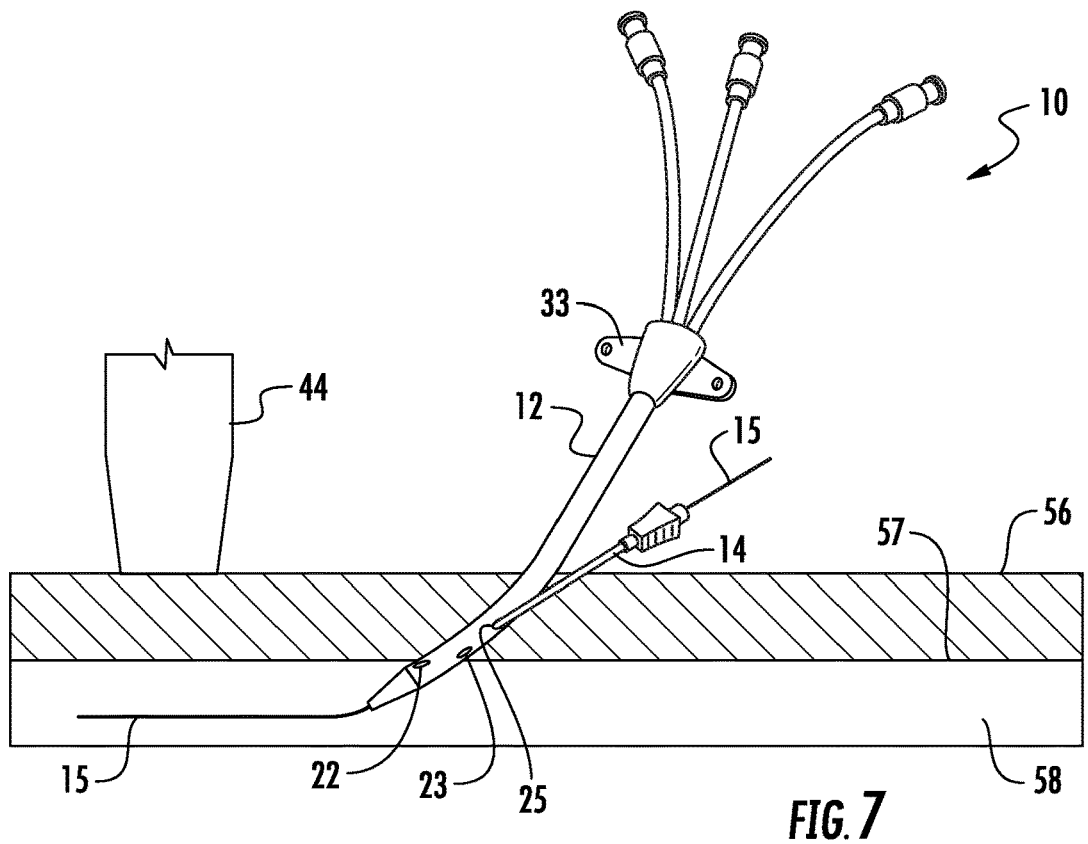
FIG. 7 is a schematic illustration of a subsequent method step of endovascular insertion of the catheter over the needle and guidewire.

FIGS. 5-8 are schematic illustrations of the method of utilizing the integrated catheter for rapid insertion. The integrated catheter assembly 10 is provided with the guidewire 15 positioned within the hollow needle 14 and the needle 14 is positioned within the side port 25. A proximal portion of the needle extends contiguous to and external of a proximal portion of the catheter 12. The distal portion of the needle 14 extends within and along the length of the transverse channel 36 and within and along the length of a distal portion of the lumen 20. The needle insertion tip 37 extends through the distal aperture of the catheter distal tip 38. As shown in FIG. 5, the needle insertion tip 37, preferably utilizing ultrasound guidance 44, penetrates the skin 56, subcutaneous tissue, and the vessel wall 57, entering the target vessel 58. As shown in FIG. 6, once penetration into the vessel is confirmed, by ultrasound or aspiration, endovascular deployment of the guidewire 15 is achieved. The physician advances the guidewire 15 by applying inward force on the proximal end of the guidewire 15, utilizing the visible markings thereon to determine depth of insertion. The physician, while fixing the needle 14 and wire 15 in place, advances the catheter over the needle and wire by applying downward pressure until the catheter 12, too, achieves intravascular placement as shown in FIG. 7.

Figure 8:
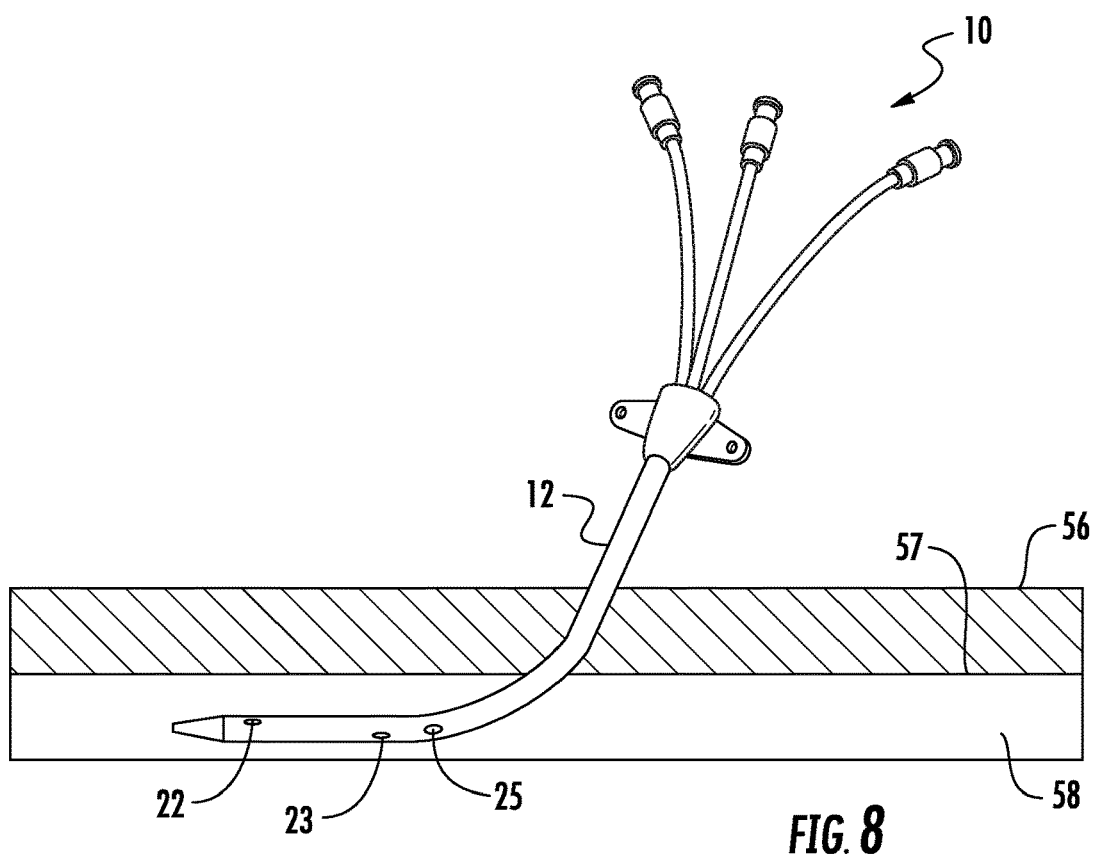
FIG. 8 is a schematic illustration of a subsequent method step of removal of the needle and guidewire from the vessel lumen and the catheter needle side port.

As shown in FIG. 8, the needle 14 and the guidewire 15 are then withdrawn. According to another aspect of the present invention, the needle 14 and guidewire 15 may be removed together, in a single step. The guidewire 15 is then withdrawn and the catheter 12 has been rapidly inserted into the endovascular system. Particularly with the use of ultrasound guidance, this method enables the catheter assembly 10 and, hence, the catheter 12, to be properly and rapidly positioned within the vasculature, without requiring multiple steps of exchanging components as in prior art methods. Moreover, the integrity of the sterile environment is maintained by virtue of utilizing fewer independent components requiring additional and independent manipulation. While not being bound by any particular theory, it is believed that the speed of infusion through the lumen is increased due to the ability of fluids to enter the vasculature from two ports: one at the distal tip 38 and one at the side port 25. It is also believed that because the effective length of the catheter lumen is decreased, at least in part due to Poiseuille's law or other principles, the flow rate is further increased. The integrated catheter assembly 10 decreases the risk of loss of venous access which may occur in prior art methods as components are exchanged. Additionally, the integrated catheter, with one or more stylets, obturates all lumens and prevents complications of air embolism and limits blood loss during insertion.

Alternative embodiments of the present invention include use of specialized antithrombogenic or antibacterial surface coatings, or composites including these, for various components of the catheter assembly. The number of lumens may vary, based upon the intended clinical use. The novel method and catheter assembly according to the present invention may be employed for other vascular access devices and procedures, including, but not limited to, temporary dialysis catheters, peripherally inserted catheters, venous and arterial sheaths, and other vascular access lines or midline catheters. Moreover, the size of various components may be varied for diverse reasons, including, the age of patient, access site, and/or anatomy. A plurality of sizes and lengths may, therefore, be provided. The catheter may be formed of materials having varying stiffness. Conventional catheters are made of a 49 durometer material on the Shore D scale, although other materials or compositions having varying stiffness may be selected, depending upon the clinical need. As described herein, the catheter assembly according to the present invention preferably is positioned utilizing ultrasound guidance. Other guidance techniques, such as fluoroscopy and computed tomography may also be employed. Other guidance techniques, such as palpation, direct visualization, or anatomical landmarks, may also be used to position the catheter assembly according to the present invention.

While exemplary embodiments have been shown and described above for the purpose of disclosure, modifications to the disclosed embodiments may occur to those skilled in the art. The disclosure, therefore, is not limited to the above precise embodiments and that changes may be made without departing from its spirit and scope.

What is claimed is:

1. An integrated catheter assembly for rapid insertion into a blood vessel, comprising:
   a needle having a guidewire disposed in a needle lumen; and
   a catheter having a first longitudinal length defined between a proximal end and a distal end, the catheter comprising:
      a longitudinally extending first lumen extending between the proximal end and the distal end, the first lumen terminating at a distal port in the distal end;
      a first lumen side port positioned between the proximal end and the distal end; and
      a generally cylindrical transverse channel having a predetermined length defined by a sidewall extending circumferentially around the first lumen side port to the first lumen at an angle transverse to a first lumen longitudinal axis, the needle and guidewire extending through the first lumen side port, the generally cylindrical transverse channel, and the distal port such that a tip of the needle extends past the distal end of the catheter and a proximal end of the needle and guidewire extend proximal to the first lumen side port for insertion of the catheter into a patient.

2. The integrated catheter assembly according to claim 1, further comprising a second longitudinally extending lumen extending from the proximal end to a second lumen side port for providing fluid communication with the second lumen for fluid administration, wherein the second lumen side port is distal to the first lumen side port.

3. The integrated catheter assembly according to claim 2, further comprising a third longitudinally extending lumen extending from the proximal end to a third lumen side port for providing open communication with the third lumen for fluid administration, wherein the third lumen side port is distal to the first lumen side port.

4. The integrated catheter assembly according to claim 3, wherein the second lumen side port, the third lumen side port, and the first lumen side port are positioned in a helical configuration around the catheter.

5. The integrated catheter assembly according to claim 1, wherein the generally cylindrical transverse channel extends from the first lumen at an acute angle.

6. The integrated catheter assembly according to claim 1, wherein the catheter has a wall thickness defined between an outer surface and the first lumen, and wherein the predetermined length of the generally cylindrical transverse channel is greater than the wall thickness.

7. The integrated catheter assembly according to claim 1, wherein the distal port is sized in accordance with a gauge of the needle.

8. The integrated catheter assembly according to claim 1, wherein the needle includes an etched portion in the form of a band to provide improved visualization when using ultrasound guidance.

9. The integrated catheter assembly according to claim 1, wherein the guidewire includes visible marks at regular intervals along a section proximal of the needle to indicate a depth of the guidewire when inserted through the needle after intravenous access.

10. The integrated catheter assembly according to claim 1, wherein the guidewire is formed as a composite with a nitinol core.

11. The integrated catheter assembly according to claim 1, further comprising a hemostatic valve configured to facilitate aspiration of the first lumen side port.

12. The integrated catheter assembly according to claim 2, further comprising a stylet configured for insertion into the second lumen to provide increased column strength of the catheter.

13. The integrated catheter assembly according to claim 3, further comprising a stylet configured for insertion into the third lumen to provide increased column strength of the catheter.

14. The integrated catheter assembly according to claim 3, further comprising a first stylet configured for insertion into the second lumen, and a second stylet configured for insertion into the third lumen, the first stylet and the second stylet configured to provide increased column strength of the catheter.

* * * * *